United States Patent [19]
Philippo et al.

[11] Patent Number: 6,063,810
[45] Date of Patent: May 16, 2000

[54] 2-AMINOETHYL-BENZOFURAN DERIVATIVES, PREPARATION THEREOF AND THERAPEUTICAL USE THEREOF

[75] Inventors: Christophe Philippo, Rueil Malmaison; Gilles Courtemanche, Saint Martin du Tertre; Eykmar Fett, Gif sur Yvette; Marie Claire Orts, Rueil Malmaison; Philippe Bovy, Mareil Marly; Stephen Eric O'Connor, Gif sur Yvette; Anne Marie Galzin, Paris, all of France

[73] Assignee: Synthelabo, Le Plessis Robinson, France

[21] Appl. No.: 09/125,947

[22] PCT Filed: Mar. 5, 1997

[86] PCT No.: PCT/FR97/00383

§ 371 Date: Aug. 31, 1998

§ 102(e) Date: Aug. 31, 1998

[87] PCT Pub. No.: WO97/32870

PCT Pub. Date: Sep. 12, 1997

[30] Foreign Application Priority Data

Mar. 8, 1996 [FR] France ................... 96 02938
Sep. 5, 1996 [FR] France ................... 96 10829

[51] Int. Cl.⁷ ........................ A61K 31/343; C07D 307/79
[52] U.S. Cl. ..................... 514/469; 549/467; 546/196; 548/525; 548/950
[58] Field of Search ..................... 514/469, 320, 514/422; 549/467, 460; 548/525, 950; 546/196

[56] References Cited

U.S. PATENT DOCUMENTS

| | | | |
|---|---|---|---|
| 4,829,067 | 5/1989 | Iijima et al. | 514/233.5 |
| 4,882,340 | 11/1989 | Iijima et al. | 514/320 |
| 5,288,749 | 2/1994 | Meyer et al. | 514/414 |
| 5,474,994 | 12/1995 | Leonardi et al. | 514/218 |

FOREIGN PATENT DOCUMENTS

| | | |
|---|---|---|
| 0 270 342 | 6/1988 | European Pat. Off. . |
| 0 306 226 | 3/1989 | European Pat. Off. . |
| 0 558 245 | 9/1993 | European Pat. Off. . |
| 0 693 475 | 1/1996 | European Pat. Off. . |
| 1532210 | 6/1968 | France . |
| WO94/20472 | 9/1994 | WIPO . |

OTHER PUBLICATIONS

Royer, R. et al.: Benzofurans. L. Access to furoisoquinolines. Bull. Soc. Chim. Fr. vol. 11, pp. 4201–4208, 1972
Chem. Pharm. Bull., vol. 40, No. 5, 1992, pp. 1148–1153.
Katritzky, A. et al, Synthesis, Sep. 1994, pp. 907–908.
J. Org. Chem., vol. 52, No. 4, 1987, pp. 491–492.
Tet. Lett., 22, 1981, p. 3815.

*Primary Examiner*—John Kight
*Assistant Examiner*—Charanjit S. Aulakh
*Attorney, Agent, or Firm*—Jacobson, Price, Holman & Stern, PLLC

[57] ABSTRACT

Compounds of formula (I), wherein A is a hydrogen atom or a hydroxyl group; B is a hydrogen atom or a $C_{1-8}$ alkyl, $C_{1-8}$ alkenyl, $C_{1-8}$ fluoroalkyl or $C_{1-8}$ perfluoroalkyl group; each of $R_1$, $R_2$ and $R_5$, which are the same or different, is a hydrogen atom, a halogen such as chlorine, bromine or fluorine, a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ taken together form a $C_{3-8}$ cycloalkyl, $C_{3-8}$ cycloalkenyl or $C_6$, $C_{10}$ or $C_{14}$ aryl ring, except for compounds in which $R_1$ and $R_2$ are both hydrogen; each of $R_3$ and $R_4$, which are the same or different, is a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ taken together form a $C_{2-6}$ cycloalkyl or $C_{3-6}$ cycloalkenyl ring, e.g., piperidyl, azetidinyl or pyrrolidyl; in the form of enantiomers, diastereoisomers or mixtures thereof, including racemic mixtures;, as well as pharmaceutically acceptable acid addition salts thereof. The compounds may be used in therapy.

14 Claims, No Drawings

2-AMINOETHYL-BENZOFURAN DERIVATIVES, PREPARATION THEREOF AND THERAPEUTICAL USE THEREOF

This application is a 371 of PCT/FR97/00383 filed Mar. 5, 1997, now WO97/32870 Sep. 12, 1997.

The subject-matter of the present invention is (2-aminoethyl)benzofuran derivatives, the preparation thereof and the therapeutical use thereof.

Patent Application WO 94 20472 discloses synthetic intermediates: 2-(benzofuran-7-yl)ethyl-N-methylamine and 2-[[2-(2,3-dimethoxyphenyl)ethyl]methylamino]-1-(benzofuran-7-yl)ethanol.

Patent FR 1,532,210 discloses heterocyclic compounds of formula:

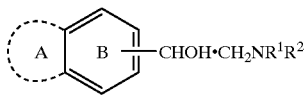

and in particular 1-(dibenzofuran-2-yl)-2-isopropylaminoethanol.

Patent Application EP 306,226 discloses benzofurans of formula:

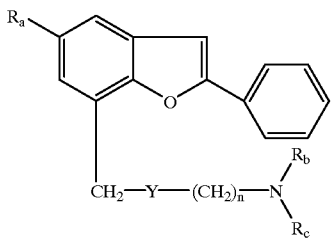

Patent Application EP 270,342 discloses benzofurans of formula:

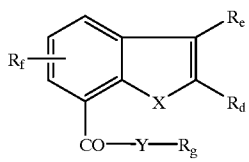

Finally, Patent Application EP 558,245 discloses a benzofuran compound: 7-{3-[4-(2-methoxyphenyl)-1-piperazinyl]propylcarbamoyl}-2-phenylbenzo[b]furan.

The (2-aminoethyl)benzofuran derivatives of the present invention correspond to the following general formula (I)

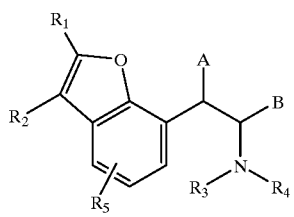

in which:
A represents either a hydrogen atom or a hydroxyl group,
B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$, $R_2$ and $R_5$, which are identical or different, each represent a hydrogen atom, a halogen, such as a chlorine, a bromine or a fluorine, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, such as, for example, a piperidyl, azetidinyl or pyrrolidyl.

The preferred compounds according to the invention are those comprising radicals having the following meanings:

$R_1$ and $R_2$ each represent a $C_1$-$C_4$ alkyl group, more preferably a methyl, ethyl or i-propyl group, or a $CF_3$ group, or $R_1$ and $R_2$ together form a $C_3$-$C_6$ cycloalkyl group, $R_3$ and $R_4$ each represent a $C_1$-$C_4$ alkyl group, more preferably a methyl, ethyl or i-propyl group, $R_5$ represents a hydrogen atom, A represents a hydroxyl group, B represents a hydrogen atom.

The compounds of the invention can be used as medicaments, as contractile agents for smooth muscles and more particularly in the treatment of urinary incontinence, or as venoconstrictors and more particularly in the treatment of venous insufficiency or of venous ulcers.

Patent FR 1,532,210 discloses a very large family of heterocyclic compounds of formula W,

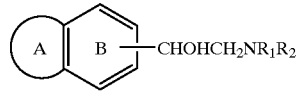

in which A represents an optionally substituted pentagonal, hexagonal or heptagonal heterocyclic nucleus comprising one or more nitrogen, oxygen and/or sulphur atoms, only 22 compounds of which are specifically disclosed. None of these 22 compounds, which constitute the preferred compounds of this patent, comprises a benzofuran nucleus. These compounds are described as agents for blocking the beta-adrenergic effect and are used in the curative or prophylactic treatment of coronary diseases.

The compounds of general formula (I) comprise one or more asymmetric carbon atoms. They can therefore exist in the form of enantiomers or of diastereoisomers. These enantiomers, diastereoisomers and their mixtures, including racemic mixtures, form part of the invention.

The pharmaceutically acceptable salts of the compounds of formula (I) according to the invention can either be salts of inorganic acids, such as hydrochloric acid, hydrobromic acid, sulphuric acid or phosphoric acid, or salts of organic acids, such as acetic acid, citric acid, tartaric acid, maleic acid, succinic acid, methanesulphonic acid or fumaric acid. Salts of hydrochloric acid are preferred.

Mention may be made, as other salts, of those of oxalic acid.

The compounds derived from (2-aminoethyl)benzofuran of formula (I) according to the invention can be prepared according to various processes. These processes are disclosed below.

1. The compounds of formula (I), in particular those in which A represents a hydroxyl group, can be prepared according to the process disclosed in the appendix.

According to this process, an aldehyde of formula II is reacted with an (aminoalkyl)stannate derivative of formula III. The meanings of $R_1$, $R_2$, $R_3$, $R_4$, $R_5$ and B of the compounds of formulae II and III are those shown in the formula I. This reaction can be carried out in an organic solvent, such as tetrahydrofuran, in the presence of n-butyllithium. 0.2 to 1.5 mol of the compound of formula II are generally reacted per one mol of the compound of formula III.

The compounds of formula III can be prepared by a person skilled in the art according to the process described by Katrizky A. R., Chang H-X. and Wu J., Synthesis, 1994, 907.

The compounds of formula II can be prepared by formulation of a brominated derivative of formula IV by means of tert-butyllithium. The formylation reaction can be carried out in an organic solvent, such as tetrahydrofuran, N,N-dimethylformamide or a mixture of these solvents. Generally, 0.8 to 1.2 mol of tert-butyllithium are employed per one mol of compound of formula IV.

The compounds of formula IV can themselves be prepared from β-phenoxyketones of formula V, which are reacted with an acid, preferably an inorganic acid, such as polyphosphoric acid or, advantageously, sulphuric acid.

The meanings of $R_1$, $R_2$ and $R_5$ in the compounds of formulae IV and V are those shown in the formula I.

The compounds of formula V can be obtained directly from the corresponding phenols of formula VI, which are reacted with an α-haloketone of formula VII. This reaction can be carried out in an organic solvent, such as N,N-dimethylformamide, in the presence of potassium carbonate and of an iodide, such as potassium iodide. The said a-haloketone is usually an α-chloroketone.

Generally, 0.2 to 2 mol of α-haloketone are reacted per one mol of compound of formula VI.

The meanings of $R_1$, $R_2$ and $R_5$ in the compounds of formulae VI and VII are those shown in the formula I.

The compounds of formula V can also be prepared by reaction of a compound of formula VI as defined above with an α-haloester of formula VIII, where $R_1$ has the meaning shown in the formula I. This reaction can be carried out in an organic solvent, such as N,N-dimethylformamide, in the presence of potassium carbonate and of an iodide, such as potassium iodide. Generally, 0.2 to 2 mol of α-haloester are reacted per one mol of compound of formula VI.

The product of this reaction is subsequently saponified by a base, such as sodium hydroxide, to form a compound of formula IX. The latter is subsequently converted to its acid chloride or its Weinreb amide by reaction with, for example, thionyl chloride ($SOCl_2$) or an $SO_2Cl_2/NHCH_3OCH_3$ mixture, under the conditions described by Nahm and Weinreb, Tet. Lett., 22, 3815, 1981. The said compound of formula V can then be prepared by reaction between the acid chloride of the compound IX or the Weinreb amide of the latter and an organometallic compound of formula X, in which $R_2$ is as defined in the formula (I) and X represents a halogen atom. This organometallic compound is preferably an organomagnesium compound.

In addition to the process described above, the compounds of formula IV, in particular those in which $R_1$ is a methyl group and $R_2$ is a hydrogen atom, can be prepared according to the following reaction scheme (1):

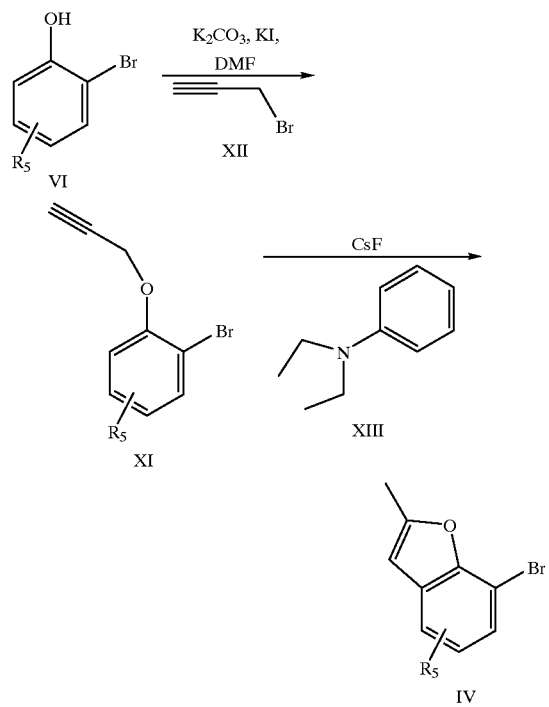

According to this process, a compound of formula VI as defined above is reacted with propargyl bromide. This reaction can be carried out in an organic solvent, such as N,N-dimethylformamide, in the presence of potassium carbonate and of an iodide, such as potassium iodide. Generally, 0.2 to 2 mol of propargyl bromide are reacted per one mol of compound of formula VI. The phenoxypropargyl derivative of formula XI thus obtained is subsequently reacted with diethylaniline in the presence of caesium fluoride, this reaction being carried out under the conditions described by Ishi H., Ishihawa T., Takeda S., Veki S. and Suzuki M., Chem. Pharm. Bull., 40, 1992, 1148.

2. The compounds of formula (I) according to the invention in which A is a hydroxyl group can also be prepared according to the following reaction scheme (2):

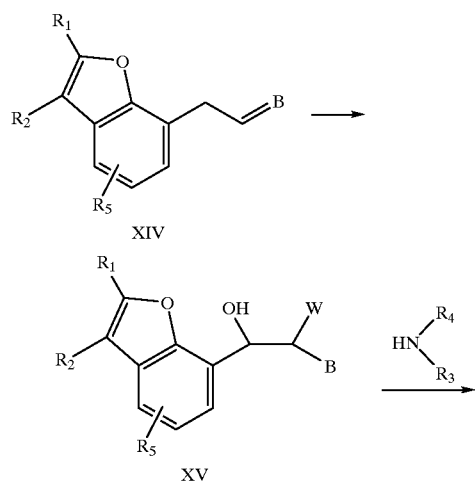

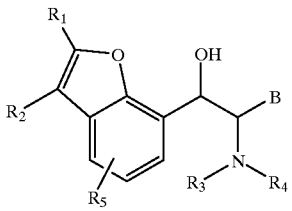

According to this process, an ethenylbenzofuran derivative of formula XIV is reacted with an oxidizing agent, such as sodium periodate, osmium tetroxide or meta-chloroperbenzoic acid, followed by hydrolysis in basic or acidic medium, so as to form a diol. The hydroxyl group in the geminal position with respect to the B group in the diol thus obtained can subsequently optionally be selectively activated, in a way known to a person skilled in the art, so as to obtain the compound of formula XV. In the latter, W represents a hydroxyl group or, when the hydroxyl group has been activated, W represents a nucleofuge group, such as a tosyl group, a mesyl group or a bromine atom.

The compound of formula (I) according to the invention is subsequently prepared from the compound of formula XV by reacting the latter with an amine $NHR_3R_4$. Usually, 0.01 to 2 mol of the compound of formula XV are reacted per one mol of the said amine. The meanings of $R_1$, $R_2$, $R_3$, $R_4$, $R_5$ and B in each of the compounds of formulae XIV and XV and in the amine $NHR_3R_4$ are those shown in the formula I.

The ethenylbenzofuran derivative of formula XIV can itself be prepared from a benzofuran of formula IV as defined above by Stille palladium coupling under the conditions defined by McKean D. R., Parinello G., Renaldo A. F. and Stille J. K., J. Org. Chem., 52, 1987, 492.

Alternatively, the ethenylbenzofuran derivative of formula XIV can be prepared from an aldehyde derivative of formula II by a Wittig reaction under conditions which are conventional for a person skilled in the art.

3. The compounds of formula (I) according to the invention in which A is a hydroxyl group can also be prepared according to the following reaction scheme (3):

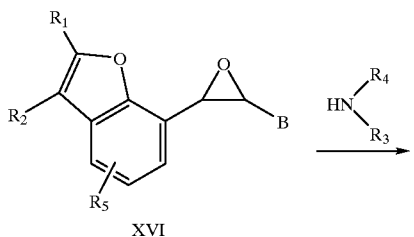

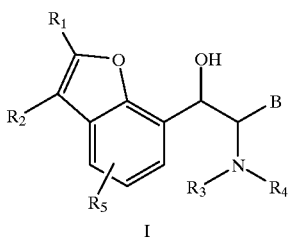

According to this process, the compound of formula (I) is prepared by reacting an oxirane derivative of formula XVI with an amine $NHR_3R_4$. The meanings of $R_1$, $R_2$, $R_3$, $R_4$, $R_5$ and B of the oxirane derivative of formula XVI and of the said amine are those shown above in the formula I.

The oxirane derivative of XVI can be prepared according to one of the following processes:

by reaction of trimethylsulphonium iodide with the aldehyde of formula II described above. To carry out this reaction, use may be made of 1 to 10 mol of trimethylsulphonium iodide per one mol of the said aldehyde of formula II.

by reaction of a peracid, such as meta-chloroperbenzoic acid, with the ethenylbenzofuran derivative of formula XIV under conditions which are conventional for a person skilled in the art.

it is also possible to obtain the oxirane from a ketone of formula XVII

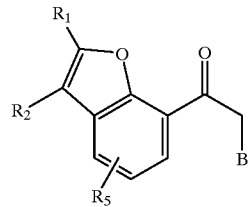

In this case, the ketone is halogenated in the α position, reduced to the halohydrin, then treated with a base and converted to the oxirane XVI.

4. The compounds of formula (I) according to the invention in which A and $R_5$ each represent a hydrogen atom can advantageously be prepared according to the following reaction scheme (4):

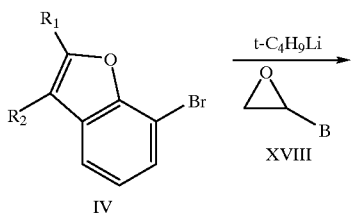

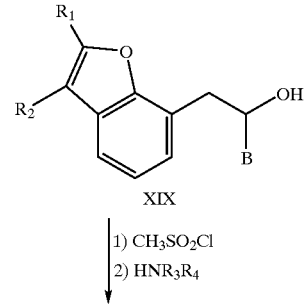

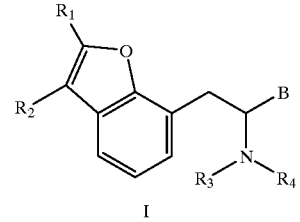

According to this process, a brominated derivative of formula IV as defined above is transmetallated, for example by means of tert-butyllithium, and then this product is reacted with an oxirane of formula XVIII, where B has one of the meanings shown in the formula I. Usually, 0.8 to 1.2 mol of brominated derivative of formula IV and 1 to 1000 mol of oxirane of formula XVIII are used per one mol of tert-butyllithium. The reaction can be carried out in an organic solvent, such as tetrahydrofuran. The compound of formula XIX obtained can subsequently be activated, for example by means of mesyl chloride (MsCl), and is then reacted with an amine $NHR_3R_4$, as defined above. Usually, 0.01 to 1 mol of compound of formula XIX is employed per one mol of the said amine.

5. The compounds of formula (I) according to the invention in which A is a hydrogen atom can also be prepared by dehydroxylation of a corresponding compound of formula (I) where A is a hydroxyl group. The dehydroxylation reaction can be carried out, in a way known to a person skilled in the art, by reaction with triethylsilane and trifluoroacetic acid.

The aim of the following examples is to illustrate the present invention.

EXAMPLE 1

Ethyl 2-(2-bromophenoxy)pentanoate 13.8 ml (119.6 mmol) of 2-bromophenol, 25 g (119.6 mmol) of ethyl 2-bromopentanoate, 19.8 g (143.3 mmol) of potassium carbonate, 19.8 g (119.6mmol) of potassium iodide and 210 ml of N,N-dimethylformamide are introduced into a 1 l three-necked flask equipped with a reflux condenser. The mixture is heated at 45° C. for 16 hours. 600 ml of water are added and extraction is carried out with ethyl acetate (3×300 ml). The combined organic phases are washed with 200 ml of a molar sodium hydroxide solution, 2×200 ml of water and 300 ml of brine. They are then dried over sodium sulphate, filtered and concentrated under vacuum and the residue is purified by silica flash chromatography (cyclohexane elution) to give 28.5 g (79%) of ethyl 2-(2-bromophenoxy)pentanoate in the form of an oil.

EXAMPLE 2

Ethyl 2-(2-bromophenoxy)butanoate

Under the conditions of Example 1 but using ethyl 2-bromobutanoate, ethyl 2-(2-bromophenoxy)butanoate was prepared in the form of a yellow oil.

EXAMPLE 3

2-(2-Bromophenoxy)pentanoic acid 26.5 g (188 mmol) of ethyl 2-(2-bromophenoxy) pentanoate, 50 ml of methanol, 21.1 g (528 mmol) of sodium hydroxide pellets and 3 ml of water are placed in 250 ml three-necked flask equipped with a reflux condenser. The mixture is heated at reflux for 3 hours and then cooled to room temperature and concentrated. 200 ml of water are added and extraction is carried out with 150 ml of petroleum ether. The aqueous phase is subsequently acidified by the addition of a hydrochloric acid solution and then extracted with 3×200 ml of chloroform. The combined organic phases are dried over magnesium sulphate, filtered and concentrated under vacuum to give 23.8 g (99% yield) of 2-(2-bromophenoxy)pentanoic acid—M.p.=63° C.

EXAMPLE 4

2-(2-Bromophenoxy)butanoic acid

Under the conditions of Example 3 but using ethyl 2-(2-bromophenoxy)butanoate, 2-(2-bromophenoxy) butanoic acid was prepared—M.p.=102° C.

EXAMPLE 5

2-(2-Bromophenoxy)pentanoic acid chloride 23.8 g (87 mmol) of 2-(2-bromophenoxy)pentanoic acid and 90 ml of thionyl chloride are placed in a 250 ml round-bottomed flask equipped with a reflux condenser. The mixture is heated at 80° C. for 4 hours. The thionyl chloride is evaporated and the residue purified by distillation under reduced pressure (0.1 millibar). 19.3 g of 2-(2-bromophenoxy)pentanoic acid chloride are obtained (76% yield); B.p.=114° C. (0.1 mb, 10 Pa).

EXAMPLE 6

2-(2-Bromophenoxy)butanoic acid chloride

Under the conditions of Example 5 but using 2-(2-bromophenoxy)butanoic acid, 2-(2-bromophenoxy)butanoic acid chloride was prepared; B.p.=100° C. (0.8 mb, 80 Pa).

EXAMPLE 7

N-Methyl-O-methyl-2-(2-bromophenoxy) pentanohydroxamic acid 5.5 g (18.9 mmol) of 2-(2-bromophenoxy)pentanoic acid chloride, 2.03 g (20.8 mmol) of N-methyl-O-methylhydroxylamine and 190 ml of dichloromethane are placed in a 500 ml round-bottomed flask. The solution is cooled to 0° C. and 5.8 ml (41.6 mmol) of triethylamine are slowly added. The solution is stirred for 1 hour at room temperature and then concentrated under vacuum. 100 ml of a molar hydrochloric acid solution are added to the residue and extraction is carried out with 3×100 ml of ethyl ether. The combined organic phases are dried over magnesium sulphate, filtered and concentrated under vacuum to give 6 g of N-methyl-O-methyl-2-(2-bromophenoxy) pentanohydroxamic acid in the form of a colourless oil; quantitative yield.

EXAMPLE 8

3-(2-Bromophenoxy)-2-hexanone 6 g of N-methyl-O-methyl-2-(2-bromophenoxy) pentanohydroxamic acid and 190 ml of anhydrous tetrahydrofuran are placed in a 500 ml round-bottomed flask. The solution is cooled to −10° C. and 19 ml of a 3M solution of methylmagnesium bromide in ether are slowly added. The mixture is stirred for 45 minutes and 60 ml of a molar hydrochloric acid solution are slowly added. The mixture is extracted with 3×100 ml of ethyl ether. The combined organic phases are dried over magnesium sulphate, filtered and concentrated under vacuum to provide 5.13 g of 3-(2-bromophenoxy)-2-hexanone in the form of a colourless oil. Quantitative yield.

EXAMPLE 9

4-(2-Bromophenoxy)-3-hexanone and 4-(2-bromophenoxy)-3-heptanone were also prepared under the conditions in Example 8, both existing in the form of a colourless oil.

EXAMPLE 10

2,3-Dimethyl-7-(2-diethylamino-1-hydroxythyl) benzofuran hemioxalate (1) 3-(2-Bromophenoxy)-2-butanone:

60 g (347 mmol) of 2-bromophenol, 57.43 g (416 mmol) of potassium carbonate, 57 g (347 mmol) of potassium iodide, 600 ml of dimethylformamide and 4.34 g (416 mmol) of 3-chloro-2-butanone are introduced into a 1 liter three-necked flask equipped with a reflux condenser. The mixture is heated to 80° C. for 16 hours. 1500 ml of water are added and then extraction is carried out with ethyl acetate (3×400 ml). The organic phases are combined, washed with a molar sodium hydroxide solution (2×500 ml), dried over magnesium sulphate and concentrated. The residue is purified by silica column chromatography (elution solvent, 9/1 cyclohexane/ethyl acetate). 75.07 g (yield: 89%) of 3-(2-bromophenoxy)-2-butanone are obtained (yellow oil).

(2) 2,3-Dimethyl-7-bromobenzofuran:

25 ml of concentrated sulphuric acid are introduced into a 100 ml three-necked flask equipped with a thermometer and a 10 ml dropping funnel and cooling is carried out to between −15 and 0° C. with a bath of solid carbon dioxide in acetone. 3-(2-Bromophenoxy)-2-butanone (5 g, 20.6 mmol) is added dropwise and stirring is continued for 5 min. The mixture is poured onto crushed ice and then extraction is carried out with ethyl acetate (3×80 ml). The organic phases are combined, dried over magnesium sulphate and concentrated. The residue is purified by silica column chromatography (elution solvent: cyclohexane). 4.24 g (Yield: 91%) of 2,3-dimethyl-7-bromobenzofuran are obtained—M.p.: 33° C.

(3) 2,3-Dimethyl-7-formylbenzofuran:

17 g (75.6 mmol) of 2,3-dimethyl-7-bromobenzofuran and 250 ml of tetrahydrofuran are introduced into a 1 liter round-bottomed flask under an inert atmosphere. The mixture is cooled to −78° C. by a bath of solid carbon dioxide in acetone. 60 ml of tert-butyllithium (1.4M in pentane) are added dropwise and the mixture is left stirring for 10 min. 17.5 ml of dimethylformamide (227 mmol) are subsequently added dropwise and the reaction mixture is allowed to return to room temperature. 100 ml of water are added and then extraction is carried out with ethyl acetate (3×80 ml). The organic phases are combined, dried over magnesium sulphate and concentrated. The residue is purified by silica column chromatography (elution solvent: 9/1 cyclohexane/ethyl acetate).

11.97 g (Yield: 91%) of 2,3-dimethyl-7-formylbenzofuran are obtained—M.p.: 56–58° C.

(4) 2,3-Dimethyl-7-(2-diethylamino-1-hydroxyethyl) benzofuran:

8.64 g (23 mmol) of 1-(N,N-diethylamino)methyltributylstannate (prepared according to the procedure of A. R. Katritzky et al., Synthesis, 1994, 907) and 35 ml of tetrahydrofuran are introduced into a 250 ml three-necked flask equipped with a 10 ml dropping funnel. Cooling is carried out to −70° C. with a bath of solid carbon dioxide in acetone. 10 ml of n-butyllithium (2.5M in hexane) are added dropwise and stirring is continued for 30 min. A solution of 2,3-dimethyl-7-formylbenzofuran (4.0 g, 23 mmol) in tetrahydrofuran (35 ml) is then added dropwise. Stirring is continued for 1 hour at −78° C. before allowing the reaction mixture to return to room temperature. 100 ml of water are added and then extraction is carried out with ethyl acetate (3×100 ml). The organic phases are combined and extracted with a 1M hydrochloric acid solution (3×100 ml). The aqueous phases are combined, basified by the addition of sodium hydroxide solution (30%, 5 ml) and extracted with ethyl ether (3×100 ml). The organic phases are combined, dried over magnesium sulphate and concentrated. The residue is purified by silica column chromatography (elution solvent: 95/5 dichloromethane/methanol).

2.8 g of 2,3-dimethyl-7-(2-diethylamino-1-hydroxyethyl) benzofuran are obtained—M.p.: 65° C.

(5) 2,3-Dimethyl-7-(2-diethylamino-1-hydroxyethyl) benzofuran hemioxalate:

The addition is carried out, to the 2,3-dimethyl-7-(2-diethylamino-1-hydroxyethyl)benzofuran obtained in Stage (4), of ½ equivalent of oxalic acid as a 2M solution in methanol and the salt is concentrated under vacuum, recrystallized from ethyl acetate and then dried in a desiccator under vacuum over phosphorus pentoxide.

2,3-Dimethyl-7-(2-diethylamino-1-hydroxyethyl) benzofuran hemioxalate is obtained—M.p.: 160° C.

EXAMPLE 11

By repeating the process of Example 10, with appropriate starting materials, other compounds of formula (I) in accordance with the invention were prepared. These compounds are those having the numbers 3 to 30 in the Table below.

However, it is noted that the compounds 12 and 13 are obtained from synthetic intermediates for the compounds 8 and 9, these synthetic intermediates having been appropriately oxidized.

EXAMPLE 12

2,3-Dimethyl-6-methoxy-7-(2-diethylamino-1-hydroxyethyl)benzofuran (1) (3-Hydroxyphenoxy)acetone This compound is obtained, according to the process described in Stage (1) of Example 1 for the preparation of 3-(2-bromophenoxy)-2-butanone, from 3-hydroxyphenol.

(3-Hydroxyphenoxy)acetone is obtained in the form of an oil (Yield: 65%).

(2) 3-Methyl-6-hydroxybenzofuran 3 g (18 mmol) of (3-hydroxyphenoxy)acetone and 400 ml of a 0.1M potassium hydroxide solution are introduced into a 1 l three-necked flask equipped with a reflux condenser. Heating is carried out at reflux for 6 hours. The reaction mixture is cooled to 5° C., a molar hydrochloric acid solution is added, in order to obtain a pH of approximately 5, and extraction is carried out with ethyl ether (3×150 ml). The organic phases are combined, dried over magnesium sulphate and concentrated. The residue is purified by silica column chromatography (elution solvent: 8/2 cyclohexane/ethyl acetate). 1.61 g of 3-methyl-6-hydroxybenzofuran are obtained—M.p.: 92° C.

(3) 2,3-Dimethyl-6-methoxybenzofuran 0.7 g (4.3 mmol) of 3-methyl-6-hydroxybenzofuran and 35 ml of tetrahydrofuran are introduced into a 50 ml three-necked flask. Cooling is carried out to −78° C. with a bath of solid carbon dioxide in acetone. 2.6 ml of lithium diisopropylamide (2.0M in tetrahydrofuran/heptane) are added dropwise and stirring is continued for 20 min. 0.535 ml of methyl iodide is then added dropwise. The reaction mixture is allowed to return to room temperature. 50 ml of water are added and then extraction is carried out with ethyl acetate (3×50 ml). The organic phases are combined, dried over magnesium sulphate and concentrated. The residue is subjected a second time to the same treatment. 0.691 g of 2,3-dimethyl-6-methoxybenzofuran is obtained in the form of an oil.

(4) 2,3-Dimethyl-6-methoxy-7-formylbenzofuran

This compound is obtained, according to the process described for the preparation of 2,3-dimethyl-7-formylbenzofuran, from the corresponding starting material.

2,3-Dimethyl-6-methoxy-7-formylbenzofuran is obtained—M.p.: 88° C. (Yield: 73° C.).

(5) 2,3-Dimethyl-6-methoxy-7-(2-diethylamino-1-hydroxyethyl)benzofuran

This compound is obtained, according to the process described for the preparation of 2-methyl-3-methyl-7-(2-diethylamino-1-hydroxyethyl)benzofuran, from the corresponding starting material. 2,3-Dimethyl-6-methoxy-7-(2-diethylamino-1-hydroxyethyl)benzofuran is obtained in the form of an oil (Yield: 70%).

(6) The addition is carried out of ½ equivalent of oxalic acid as a 2M solution in methanol and the salt is concentrated under vacuum, recrystallized from ethyl acetate and then dried in a desiccator under vacuum over phosphorus pentoxide. 2,3-Dimethyl-6-methoxy-7-(2-diethylamino-l-hydroxyethyl)benzofuran hemioxalate is obtained—M.p.: 55° C.

EXAMPLE 13

2-Methyl-7-(2-diethylamino-1-hydroxyethyl)benzofuran (1) 2-Bromo-1-(propargyloxy)benzene 10 ml (86.7 mmol) of 2-bromophenol, 14.37 g (109 mmol) of potassium carbonate, 200 ml of dimethylformamide and 11.58 ml (109 mmol) of an 80% solution of propargyl bromide in hexane are introduced into a 500 ml three-necked flask equipped with a reflux condenser. The mixture is heated at 80° C. for 16 hours. 600 ml of water are added and then extraction is carried out with ethyl acetate (3×200 ml). The organic phases are combined, washed with a molar sodium hydroxide solution (2×150 ml), dried over magnesium sulphate and concentrated. The residue is purified by silica column chromatography (elution solvent: 8/2 cyclohexane/ethyl acetate).

20 g (Yield: 99%) of 2-bromo-1-(propargyloxy)benzene are obtained (yellow oil).

(2) 2-Methyl-7-bromobenzofuran 20 g (86.7 mmol) of 2-bromo-1-(propargyloxy)benzene, 18.43 g (121 mmol) of caesium fluoride and 160 ml of diethylaniline are introduced into a 1 liter three-necked flask equipped with a reflux condenser. The mixture is heated to reflux for 1 hour. 400 ml of ethyl ether are added to the mixture, which has been cooled to room temperature, and filtration is carried out. The organic phase is combined, washed with a 5% hydrochloric acid solution (2×150 ml), dried over magnesium sulphate and concentrated. The residue is purified by silica column chromatography (elution solvent: 10% ethyl acetate in cyclohexane).

5.8 g (Yield: 32%) of 2-methyl-7-bromobenzofuran are obtained in the form of an oil.

(3) 2-Methyl-7-formylbenzofuran

This compound is obtained, by the process described in Stage (3) of Example 1, by using 2-methyl-7-bromobenzofuran as starting material.

2-Methyl-7-formylbenzofuran is obtained in the form of an oil (Yield: 82%).

(4) 2-Methyl-7-(2-diethylamino-1-hydroxyethyl)benzofuran

This compound is obtained, by the process described in Stage (4) of Example 1, by using 2-methyl-7-formylbenzofuran as starting material.

2-Methyl-7-(2-diethylamino-1-hydroxyethyl)benzofuran (Compound 31) is obtained in the form of a wax (Yield: 30%).

(5) 2-Methyl-7-(2-diethylamino-1-hydroxyethyl)benzofuran hemioxalate

This compound (Compound 32) is obtained by the process described in Stage (5) of Example 1—M.p.: 172–174° C. (Yield: 66%).

EXAMPLE 14

7-(2-Diethylamino-1-hydroxyethyl)benzofuran (1) 7-Formyl-2,3-dihydrobenzofuran 108 ml of an n-butyllithium solution (2.1M) in hexane and 26.7 g (230 mmol) of tetramethylethylenediamine (TMEDA) are introduced into a 1 liter round-bottomed flask. The mixture is stirred at room temperature for 15 minutes and 23 g (190 mmol) of 2,3-dihydrobenzofuran are added. The mixture is stirred for 4 hours at 35° C., cooled to −78° C. and 13.9 g (190 mmol) of dimethylformamide are added. The temperature is allowed to return to 20° C., 500 ml of water are added and extraction is carried out with ethyl acetate (3×200 ml). The organic phases are combined, dried and concentrated under vacuum. The residue is purified by silica flash chromatography (elution: 5% ethyl acetate in petroleum ether). 9.85 g (Yield: 35%) of 7-formyl-2,3-dihydrobenzofuran are obtained—M.p.: 55° C.

(2) 7-Formylbenzofuran 0.950 g (6.4 mmol) of 7-formyl-2,3-dihydrobenzofuran, 1.82 g (8 mmol) of 2,3-dichloro-5,6-dicyanocyclohexa-2,5-diene-1,4-dione (DDQ) and 30 ml of dioxane are introduced into a 100 ml three-necked flask equipped with a reflux condenser. Heating is carried out at reflux for 24 hours. 100 ml of a molar sodium hydroxide solution are added and extraction is carried out with ethyl ether (3×80 ml). The organic phases are combined, dried and concentrated under vacuum. The residue is purified by silica flash chromatography (elution: 5% ethyl acetate in petroleum ether). 215 mg of 7-formylbenzofuran are obtained in the form of a yellow oil (Yield: 23%).

(3) 7-(2-Diethylamino-1-hydroxyethyl)benzofuran

By repeating the process described in Stage (4) of Example 1, using 7-formylbenzofuran as starting material, 7-(2-diethylamino-1-hydroxyethyl)benzofuran is obtained in the form of a wax (Yield: 43%).

By repeating the process described in Example 2, 7-(2-diethylamino-1-hydroxyethyl)benzofuran hydrochloride is prepared—M.p.: 116° C. (Yield: 70%).

EXAMPLE 15

Asymmetric synthesis of (+)-2,3-dimethyl-7-(2-diethylamino-1(S)-hydroxyethyl)benzofuran (1) 2,3-Dimethyl-7-ethenylbenzofuran 32 g (142 mmol) of 2,3-dimethyl-7-bromobenzofuran, 3.3 g (2.84 mmol) of tetrakis(triphenylphosphine)palladium, 300 ml of toluene and 50 g (156.2 mmol) of tributylvinylstannane are introduced into a 1 l three-necked flask equipped with a reflux condenser. The mixture is heated at reflux for 3 hours, 1 g of tetrakis(triphenylphosphine)palladium is added and heating is continued for 2 hours. The reaction mixture is allowed to return to room temperature and then 500 ml of ethyl acetate and 500 ml of aqueous sodium hydroxide solution are added. The organic phase is washed with brine, dried over magnesium sulphate and concentrated. The residue is distilled under a vacuum of 0.03 mm of Hg. The fraction distilling between 60 and 78° C. is collected and is subsequently purified by silica column chromatography (elution solvent: 1% ethyl acetate in cyclohexane). 13.5 g of 2,3-dimethyl-7-ethenylbenzofuran are obtained in the form of a colourless oil.

(2) (+)-2,3-Dimethyl-7-(2-hydroxy-1(S)-hydroxyethyl) benzofuran 100 g (71.43 mmol) of AD-mix-α (complex based on $K_2OsO_2(OH)_4$, on $Fe(CN)_6$ and, as ligand, on hydroquinine 1,4-phthalazinediyl diether), 358 ml of water and 358 ml of tert-butanol are introduced into a 2 l three-necked flask equipped with a thermometer. The mixture is stirred at room temperature for 15 min, in order to homogenize it, and then cooled to 0° C. 12.3 g (71.5 mmol) of 2,3-dimethyl-7-ethenylbenzofuran are added and the reaction mixture is stirred at 0° C. for 6 h. 200 ml of water and 72 g of sodium sulphite are added, stirring is carried out for 1 h at room temperature and extraction is carried out with ethyl acetate (2×600 ml). The organic phases are combined, washed with brine, dried over magnesium sulphate and concentrated. The residue is purified by silica column chromatography (elution solvent: 40% ethyl acetate in cyclohexane).

14 g of (+)-2,3-dimethyl-7-(2-hydroxy-1(S)-hydroxyethyl)benzofuran are obtained in the form of a colourless oil.

(3) (+)-2,3-Dimethyl-7-(2-para-methylphenylsulphonyl-1(S)-hydroxyethyl)benzofuran 14 g (67.96 mmol) of (+)-2,3-dimethyl-7-(2-hydroxy-1(S)-hydroxyethyl)benzofuran and 250 ml of pyridine are introduced into a 500 ml three-necked flask. The mixture is cooled to 0° C. and 11.62 g (61.16 mmol) of tosyl chloride and then 0.5 g of dimethylaminopyridine are added. The reaction mixture is stirred for 2 h at room temperature, 0.645 g of tosyl chloride is added and stirring is continued for 16 h. The mixture is cooled to 0° C. and 300 ml of ethyl acetate and then 250 ml of a hydrochloric acid solution (4M) are added. Extraction is carried out with ethyl acetate (2×400 ml). The organic phases are combined, washed with 2×250 ml of a hydrochloric acid solution (4M), dried over magnesium sulphate and concentrated. The residue is purified by silica column chromatography (elution solvent: 25% ethyl acetate in cyclohexane). 15 g of (+)-2,3-dimethyl-7-(2-para-methylphenylsulphonyl-1(S)-hydroxyethyl)benzofuran are obtained in the form of a white solid—M.p.: 90° C.

(4) (+)-2,3-Dimethyl-7-(2-diethylamino-1(S)-hydroxyethyl)benzofuran 15 g (41.65 mmol) of (+)-2,3-dimethyl-7-(2-para-methylphenylsulphonyl-1(S)-hydroxyethyl)benzofuran and 210 ml (2.03 mol) of diethylamine are introduced into a 500 ml three-necked flask equipped with a stirrer and a reflux condenser. The solution is stirred at reflux for 16 h and the solution is concentrated. The residue is purified by successive column chromatography operations (elution solvent: 90/10 dichloromethane/methanol) and dried in a desiccator under vacuum over phosphorus pentoxide. 57.4 g of (+)-2,3-dimethyl-7-(2-diethylamino-1(S)-hydroxyethyl) benzofuran are obtained in the wax form $-[\alpha]_D^{20}=+94.7°$ (c=1, methanol). The enantiomeric excess is 98.5%.

An excess of an ethanol solution saturated with anhydrous hydrochloric acid is added and the salt is concentrated under vacuum, recrystallized from ethyl acetate and then dried in a desiccator under vacuum over phosphorus pentoxide.

(+)-2,3-Dimethyl-7-(2-diethylamino-1(S)-hydroxyethyl) benzofuran hydrochloride is obtained $-[\alpha]_D^{20}=+84°$ (c=1, methanol)—M.p.: 143° C.

EXAMPLE 16

Asymmetric synthesis of (−)-2,3-dimethyl-7-(2-diethylamino-1(R)-hydroxyethyl)benzofuran Stages 1 to 4 of Example 15 were repeated, using, however, AD-mix-β (complex based on $K_2OsO_2(OH)_4$, on $Fe(CN)_6$ and, as ligand, on hydroquinidine 1,4-phthalazinediyl diether) instead of AD-mix-α in Stage 2. The following compounds were then obtained:

Stage (2): (−)-2,3-dimethyl-7-(2-hydroxy-1(R)-hydroxyethyl)benzofuran, in the form of a colourless oil, Stage (3): (−)-2,3-dimethyl-7-(2-para-methylphenylsulphonyl-1(R)-hydroxyethyl)benzofuran, in the form of a white solid—M.p.: 90° C., Stage (4): i) (−)-2,3-dimethyl-7-(2-diethylamino-1(R)-hydroxyethyl)benzofuran, in the wax form $-[\alpha]_D^{20}=-89°$ (c=1, methanol), enantiomeric excess: 97.6%, ii) (−)-2,3-dimethyl-7-(2-diethylamino-1(R)-hydroxyethyl)benzofuran hydrochloride $-[\alpha]_D^{20}=-85.3°$ (c=1, methanol)—M.p.: 138–142° C.

EXAMPLE 17

(1) 2, 3-Dimethyl-7-oxiranylbenzofuran 16.93 g (83 mmol) of trimethylsulphonium iodide, 9.3 g (166 mmol) of potassium hydroxide pellets, 0.37 ml of water and 200 ml of acetonitrile are introduced into a 500 ml round-bottomed flask equipped with a stirrer and a reflux condenser. The mixture is heated at 60° C. for 10 minutes and then a solution of 6.2 g (35 mmol) of 2,3-dimethyl-7-formylbenzofuran in 50 ml of acetonitrile is added. Heating is continued for 3 hours and the mixture is allowed to return to room temperature. 200 ml of ether are added and the reaction mixture is filtered. The ether is evaporated under vacuum and extraction is carried out with pentane (3×150 ml). The pentane fractions are combined, dried over magnesium sulphate and concentrated.

5.2 g (Yield: 94%) of 2,3-dimethyl-7-oxiranylbenzofuran are obtained (colourless oil).

(2) 2,3-Dimethyl-7-(2-diethylamino-1-hydroxyethyl) benzofuran 5.33 g (28.2 mmol) of 2,3-dimethyl-7-oxiranylbenzofuran and 20 ml (220 mmol) of diethylamine are introduced into a 100 ml round-bottomed flask equipped with a stirrer and a reflux condenser. The solution is stirred at reflux for 16 h and the solution is concentrated. The residue is purified by column chromatography (elution solvent: 90/9 dichloromethane/methanol) and dried in a desiccator under vacuum over phosphorus pentoxide.

1.41 g of 2,3-dimethyl-7-(2-diethylamino-1-hydroxyethyl)benzofuran are obtained—M.p.: 65° C.

The addition is carried out, to the compound thus obtained, of ½ equivalent of oxalic acid as a 2M solution in methanol. The salt obtained is concentrated under vacuum, recrystallized from ethyl acetate and then dried in a desiccator under vacuum over phosphorus pentoxide.

2,3-Dimethyl-7-(2-diethylamino-1-hydroxyethyl) benzofuran hemioxalate is obtained—M.p.: 160° C.

EXAMPLE 18

By using essentially the same process as that in Example 17, using an appropriate amine in Stage 2, other compounds of formula (I) in accordance with the invention were prepared. These compounds are those having the numbers 41 to 52 in the Table below.

EXAMPLE 19

2,3-Dimethyl-7-(2-amino-1-hydroxyethyl) benzofuran 1 g (4 mmol) of 2,3-dimethyl-7-(2-allylamino-1-hydroxyethyl)benzofuran, 85 mg (0.092 mmol) of Wilkinson's catalyst (tris(triphenylphosphine)rhodium(I)) and 25 ml of an acetonitrile/water (84/16) mixture are introduced into a 100 ml three-necked flask equipped with a distillation system and a 50 ml dropping funnel. 30 ml of the same acetonitrile/water (84/16) mixture are placed in the dropping funnel. The solution is stirred at reflux, under a nitrogen stream, for 1 h 30, small amounts of acetonitrile/water (84/16) mixture being added regularly in order to replace the solvent distilled off. The mixture is subsequently concentrated under vacuum and the residue is purified by column chromatography (elution solvent: 90/10 dichloromethane/methanol) and then dried in a desiccator under vacuum over phosphorus pentoxide. 354 mg of 2,3-dimethyl-7-(2-amino-1-hydroxyethyl)benzofuran are obtained—M.p.: 73° C.

The addition is carried out of ½ equivalent of oxalic acid as a 2M solution in methanol and the salt is concentrated under vacuum, recrystallized from ethyl acetate and then dried in a desiccator under vacuum over phosphorus pentoxide.

2,3-Dimethyl-7-(2-amino-1-hydroxyethyl)benzofuran oxalate is obtained—M.p.: 181° C.

EXAMPLE 20

2-Ethyloxycarbonyl-3-methyl-7-(2-diethylamino-1-hydroxyethyl)benzofuran (1) 2-Ethyloxycarbonyl-3-methyl-7-bromobenzofuran This compound is prepared from 2-bromophenol according to the procedure of Boehme W. R., Organic Synthesis, Coll. Vol. IV, 590.

(2) 2-Ethyloxycarbonyl-3-methyl-7-ethenylbenzofuran

This compound is obtained according to the process described in Example 6 for the preparation of 2,3-dimethyl-7-ethenylbenzofuran, by using 2-ethyloxycarbonyl-3-methyl-7-bromobenzofuran as starting material.

(3) 2-Ethyloxycarbonyl-3-methyl-7-oxiranylbenzofuran 610 mg (2.65 mmol) of 2-ethyloxycarbonyl-3-methyl-7-ethenylbenzofuran and 5 ml of chloroform are introduced into a 25 ml three-necked flask. The mixture is cooled to 0° C. and 480 mg (2.8 mmol) of meta-chloroperbenzoic acid (m-CPBA) are added portionwise. The mixture is stirred for 3 hours, 480 mg (2.8 mmol) of m-CPBA are again added and stirring is continued for 1 hour. 30 ml of dichloromethane are added and the mixture is filtered. The filtrate is washed with a molar sodium hydroxide solution (10 ml) and with water (2×10 ml), dried over magnesium sulphate and concentrated under vacuum. The residue is purified by silica column chromatography (elution solvent: 80% ethyl acetate in petroleum ether).

330 mg of 2-ethyloxycarbonyl-3-methyl-7-oxiranylbenzofuran are obtained in the form of a wax (Yield: 51%).

(4) 2-Ethyloxycarbonyl-3-methyl-7-(2-diethylamino-1-hydroxyethyl)benzofuran

The preparation is carried out according to Stage (2) of Example 17, 2-ethyloxycarbonyl-3-methyl-7-oxiranylbenzofuran being employed. 2-Ethyloxycarbonyl-3-methyl-7-(2-diethylamino-1-hydroxyethyl)benzofuran is then obtained in the form of a wax.

An excess of an ethanol solution saturated with anhydrous hydrochloric acid is added and the salt is concentrated under vacuum, recrystallized from ethyl acetate and then dried in a desiccator under vacuum over phosphorus pentoxide. 2-Ethyloxycarbonyl-3-methyl-7-(2-diethylamino-1-hydroxyethyl)benzofuran hydrochloride is obtained—M.p.: 190° C.

EXAMPLE 21

2,3-Dimethyl-7-(2-(diethylamino)ethyl)benzofuran (1) 2,3-Dimethyl-7-(2-hydroxyethyl)benzofuran 10 g (44.2 mmol) of 2,3-dimethyl-7-bromobenzofuran and 100 ml of tetrahydrofuran are introduced into a 500 ml round-bottomed flask which is equipped with a reflux condenser containing solid carbon dioxide and which is under an inert atmosphere. The mixture is cooled to −78° C. with a bath of solid carbon dioxide in acetone. 29 ml of tert-butyllithium (1.7M in pentane) are added dropwise and the mixture is left stirring for 10 min. Approximately 150 ml of ethylene oxide are subsequently added dropwise, the reaction mixture being allowed to return to room temperature. The reaction mixture is concentrated and the residue is purified by silica column chromatography (elution solvent: 7/3 cyclohexane/ethyl acetate).

5.18 g (Yield: 61%) of 2,3-dimethyl-7-(2-hydroxyethyl) benzofuran are obtained in the form of an oil.

(2) 2,3-Dimethyl-7-(2-(diethylamino)ethyl)benzofuran 5.1 g (26.5 mmol) of 2,3-dimethyl-7-(2-hydroxyethyl) benzofuran, 5.91 ml (42.5 mmol) of triethylamine and 500 ml of anhydrous ethyl ether are introduced, under an inert atmosphere, into a 1 l round-bottomed flask. The mixture is cooled to −30° C. and 3.3 ml (42.5 mmol) of mesyl chloride are added dropwise. The reaction mixture is stirred for 1 h 30, while being allowed to return to 0° C. 200 ml of water are added and extraction is carried out with ethyl ether. The organic phases are combined and concentrated under vacuum. 7.48 g of 2,3-dimethyl-7-(2-(methylsulphonyl) ethyl)benzofuran are obtained in the form of an oil. 7.18 g (26 mmol) of 2,3-dimethyl-7-(2-(methylsulphonyl)ethyl) benzofuran and 200 ml of diethylamine are introduced into a 500 ml round-bottomed flask equipped with a reflux condenser. The reaction mixture is stirred for 16 h at reflux and concentrated under vacuum and the residue is purified by silica column chromatography (elution solvent: 9/1 dichloromethane/methanol).

6.7 g of 2,3-dimethyl-7-(2-(diethylamino)ethyl) benzofuran are obtained in the form of a wax.

The addition is carried out of ½ equivalent of oxalic acid as a 2M solution in methanol and the salt is concentrated under vacuum, recrystallized from ethyl acetate and then dried in a desiccator under vacuum over phosphorus pentoxide.

2,3-Dimethyl-7-(2-(diethylamino)ethyl)benzofuran hemioxalate is obtained—M.p.: 158–160° C.

An excess of an ethanol solution saturated with anhydrous hydrochloric acid is added and the salt is concentrated under vacuum, recrystallized from ethyl acetate and then dried in a desiccator under vacuum over phosphorus pentoxide.

2,3-Dimethyl-7-(2-(diethylamino)ethyl)benzofuran hydrochloride is obtained—M.p.: 192° C.

EXAMPLE 22

Synthesis of 2-ethyl-3-phenyl-7-(2-(diethylamino) ethyl)benzofuran 180 mg (0.53 mmol) of 2-ethyl-3-phenyl-7-(2-diethylamino-1-hydroxyethyl)benzofuran, 1 ml of triethylsilane and 1 ml of trifluoroacetic acid are introduced into a 25 ml three-necked flask equipped with a reflux condenser. The mixture is stirred for 2 hours at room temperature and then 2 ml of triethylsilane and 1 ml of trifluoroacetic acid are added. The mixture is heated at 70° C. for 48 hours. Potassium carbonate and ethyl ether (30 ml) are added and the mixture is filtered. The filtrate is concentrated under vacuum and the residue is purified by silica column chromatography (elution solvent: 5% methanol in dichloromethane). 80 mg of 2-ethyl-3-phenyl-7-(2-(diethylamino)ethyl)benzofuran are obtained in the form of a wax.

An excess of an ethanol solution saturated with anhydrous hydrochloric acid is added and the salt is concentrated under vacuum, recrystallized from ethyl acetate and then dried in a desiccator under vacuum over phosphorus pentoxide.

2-Ethyl-3-phenyl-7-(2-(diethylamino)ethyl)benzofuran hydrochloride is thus obtained—M.p.: 168–169° C.

EXAMPLE 23

Synthesis of 2-pentafluoroethyl-3-methyl-7-(2-diethylamino-1-hydroxyethyl)benzofuran hydrochloride (1) 2-Hydroxymethyl-3-methyl-7-bromobenzofuran 51.82 ml of a 1.5 molar solution of DIBAL-H in toluene are added dropwise to a solution, cooled to −78° C. with a bath of solid carbon dioxide and acetone, of 10 g (35.3 mmol) of 2-ethyloxycarbonyl-3-methyl-7-bromobenzofuran in 100 ml of toluene. The solution is allowed to return to room temperature and 50 ml of water and 100 ml of a saturated solution of Rochelle salt are successively added. Extraction is carried out with ethyl acetate (3×80 ml). The organic phases are combined, dried over magnesium sulphate and concentrated. The residue is purified by silica column chromatography (elution solvent: 2% methanol in dichloromethane). 6.3 g (Yield: 74%) of 2-hydroxymethyl-3-methyl-7-bromobenzofuran are obtained—M.p.: 103° C.

(2) 2-Formyl-3-methyl-7-bromobenzofuran 0.7 g (7.92 mmol) of manganese dioxide is added to a solution of 0.38 g (1.58 mmol) of 2-hydroxymethyl-3-methyl-7-bromobenzofuran in 10 ml of dichloromethane. The solution is stirred at room temperature for 16 h and 0.7 g (7.92 mmol) of manganese dioxide is again added. After stirring for 24 h at room temperature, the manganous precipitate is filtered off and the filtrate is concentrated under vacuum. The residue is purified by silica column chromatography (elution solvent: 10% ethyl acetate in cyclohexane). 0.25 g (Yield: 66%) of 2-formyl-3-methyl-7-bromobenzofuran is obtained in the form of a yellow wax.

(3) 2-(2,2,2-Trifluoro-1-hydroxyethyl)-3-methyl-7-bromobenzofuran 14 mg of tetrabutylammonium fluoride and 1.22 ml of trifluoromethyltrimethylsilane, dropwise, are added to a solution, cooled to 0° C. with an ice bath, of 1.58 g (6.6 mmol) of 2-formyl-3-methyl-7-bromobenzofuran in 60 ml of THF. The solution is left stirring for 30 min at 0° C. and then for 1 h at room temperature and a solution of 6 ml of THF and of 3 ml of hydrochloric acid (3M) is added. Stirring is continued for 2 h at room temperature, 100 ml of water are added and extraction is carried out with ethyl acetate (3×60 ml). The organic phases are combined, dried over magnesium sulphate and concentrated. 198 g (Yield: 97%) of 2-(2,2,2-trifluoro-1-hydroxyethyl)-3-methyl-7-bromobenzofuran are obtained—M.p.: 93° C.

(4) 2-(2,2,2-Trifluoroacetyl)-3-methyl-7-bromobenzofuran 5.6 g (64 mmol) of manganese dioxide are added to a solution of 1.98 g (6.4 mmol) of 2-(2,2,2-trifluoro-1-hydroxyethyl)-3-methyl-7-bromobenzofuran in 60 ml of dioxane. The solution is heated at reflux for 24 h and a further 5.6 g (64 mmol) of manganese dioxide are added. After refluxing for 24 h, the manganous precipitate is filtered off and the filtrate is concentrated under vacuum. The residue is purified by silica column chromatography (elution solvent: dichloromethane).

0.82 g (Yield: 52%) of 2-(2,2,2-trifluoroacetyl)-3-methyl-7-bromobenzofuran is obtained in the form of a wax (0.37 g of unreacted 2-(2,2,2-trifluoro-1-hydroxyethyl)-3-methyl-7-bromobenzofuran is recovered).

(5) 2-Pentafluoroethyl-3-methyl-7-bromobenzofuran 0.76 ml (5.7 mmol) of DAST (diethylaminosulphur trifluoride) is added to a solution of 0.80 g (2.6 mmol) of 2-(2,2,2-trifluoroacetyl)-3-methyl-7-bromobenzofuran in 13 ml of glyme. The solution is heated at 70° C. for 16 h and 0.4 ml of DAST is added. After stirring for 6 h at 70° C., the solution is poured onto crushed ice, 50 ml of a saturated sodium bicarbonate solution are added and extraction is carried out with ethyl acetate (3×60 ml). The organic phases are combined, dried over magnesium sulphate and concentrated. The residue is purified by silica column chromatography (elution solvent: 10% ethyl acetate in cyclohexane). 0.5 g (Yield: 65%) of 2-pentafluoroethyl-3-methyl-7-bromobenzofuran is obtained—M.p.: 65° C.

(6) 2-Pentafluoroethyl-3-methyl-7-formylbenzofuran

By repeating the process described in Stage (3) of Example 10 and by using 2-pentafluoroethyl-3-methyl-7-bromobenzofuran as starting material, 2-pentafluoroethyl-3-methyl-7-formylbenzofuran is obtained in the form of a yellow solid (yield 64%)—M.p.: 78° C.

(7) 2-Pentafluoroethyl-3-methyl-7-(2-diethylamino-1-hydroxyethyl)benzofuran

By repeating the process described in Stage (4) of Example 10 and by using 2-pentafluoroethyl-3-methyl-7-formylbenzofuran as starting material, 2-pentafluoroethyl-3-methyl-7-(2-diethylamino-1-hydroxyethyl)benzofuran is obtained (yield 52%) in the form of a wax.

(8) 2-Pentafluoroethyl-3-methyl-7-(2-diethylamino-1-hydroxyethyl)benzofuran hydrochloride By repeating the process described in Stage (5) of Example 10 and by using 2-pentafluoroethyl-3-methyl-7-(2-diethylamino-1-hydroxyethyl)benzofuran as starting material, 2-pentafluoroethyl-3-methyl-7-(2-diethylamino-1-hydroxyethyl)benzofuran hydrochloride is obtained in the form of a white solid (yield 85%)—M.p.: 111° C.

The structures of the compounds which can be used according to the invention are illustrated in the Table below.

TABLE

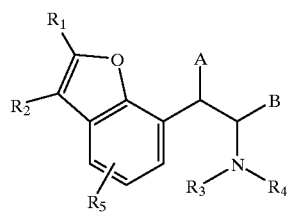

| No. | $R_1$ | $R_2$ | $R_3$ | $R_4$ | $R_5$ | A | B | Salt | M.p. (°C.) |
|---|---|---|---|---|---|---|---|---|---|
| 1 | $CH_3$ | $CH_3$ | $C_2H_5$ | $C_2H_5$ | H | OH | H | — | 65 |
| 2 | $CH_3$ | $CH_3$ | $C_2H_5$ | $C_2H_5$ | H | OH | H | Oxal | 160 |
| 3 | $CH_3$ | $CH_3$ | $C_2H_5$ | $C_2H_5$ | H | OH | H | HCl | 136 |
| 4 | $C_2H_5$ | $CH_3$ | $C_2H_5$ | $C_2H_5$ | H | OH | H | — | 42 |
| 5 | $C_2H_5$ | $CH_3$ | $C_2H_5$ | $C_2H_5$ | H | OH | H | Oxal | 143–144 |
| 6 | $iC_3H_7$ | $CH_3$ | $C_2H_5$ | $C_2H_5$ | H | OH | H | — | wax |
| 7 | $iC_3H_7$ | $CH_3$ | $C_2H_5$ | $C_2H_5$ | H | OH | H | Oxal | 146–147 |
| 8 | —$(CH_2)_4$— | | $C_2H_5$ | $C_2H_5$ | H | OH | H | — | oil |
| 9 | —$(CH_2)_4$— | | $C_2H_5$ | $C_2H_5$ | H | OH | H | Oxal | 136–136 |
| 10 | $C_6H_5$ | $C_6H_5$ | $C_2H_5$ | $C_2H_5$ | H | OH | H | — | wax |
| 11 | $C_6H_5$ | $C_6H_5$ | $C_2H_5$ | $C_2H_5$ | H | OH | H | HCl | 225 |
| 12 | —$(CH=CH)_2$— | | $C_2H_5$ | $C_2H_5$ | H | OH | H | — | wax |
| 13 | —$(CH=CH)_2$— | | $C_2H_5$ | $C_2H_5$ | H | OH | H | Oxal | 138 |
| 14 | $C_2H_5$ | $C_6H_5$ | $C_2H_5$ | $C_2H_5$ | H | OH | H | — | 107 |
| 15 | $C_2H_5$ | $C_6H_5$ | $C_2H_5$ | $C_2H_5$ | H | OH | H | HCl | 206 |
| 16 | $CH_3$ | $CH_3$ | $C_2H_5$ | $C_2H_5$ | 4 F | OH | H | — | wax |
| 17 | $CH_3$ | $CH_3$ | $C_2H_5$ | $C_2H_5$ | 4 F | OH | H | HCl | 176–174 |
| 18 | $CH_3$ | $CH_3$ | $C_2H_5$ | $C_2H_5$ | 5 F | OH | H | — | wax |
| 19 | $CH_3$ | $CH_3$ | $C_2H_5$ | $C_2H_5$ | 5 F | OH | H | HCl | 158–160 |
| 20 | $CH_3$ | $CH_3$ | $C_2H_5$ | $C_2H_5$ | 5 $CH_3$ | OH | H | — | 162 |
| 21 | $CH_3$ | $CH_3$ | $C_2H_5$ | $C_2H_5$ | 5 $CH_3$ | OH | H | HCl | 183–184 |
| 22 | $CH_3$ | $CH_3$ | $C_2H_5$ | $C_2H_5$ | 5 Cl | OH | H | — | 59 |
| 23 | $CH_3$ | $CH_3$ | $C_2H_5$ | $C_2H_5$ | 5 Cl | OH | H | HCl | 192–193 |
| 24 | $C_2H_5$ | $iC_3H_7$ | $C_2H_5$ | $C_2H_5$ | H | OH | H | — | wax |
| 25 | $C_2H_5$ | $iC_3H_7$ | $C_2H_5$ | $C_2H_5$ | H | OH | H | HCl | 129–130 |
| 26 | $C_2H_5$ | $C_2H_5$ | $C_2H_5$ | $C_2H_5$ | H | OH | H | — | 41 |
| 27 | $C_2H_5$ | $C_2H_5$ | $C_2H_5$ | $C_2H_5$ | H | OH | H | HCl | 137-138 |
| 28 | $nC_3H_7$ | $C_2H_5$ | $C_2H_5$ | $C_2H_5$ | H | OH | H | — | 114 |
| 29 | $nC_3H_7$ | $CH_3$ | $C_2H_5$ | $C_2H_5$ | H | OH | H | — | wax |
| 30 | $nC_3H_7$ | $CH_3$ | $C_2H_5$ | $C_2H_5$ | H | OH | H | HCl | 128 |
| 31 | $CH_3$ | $CH_3$ | $C_2H_5$ | $C_2H_5$ | 6-$OCH_3$ | OH | H | — | oil |
| 32 | $CH_3$ | $CH_3$ | $C_2H_5$ | $C_2H_5$ | 6-$OCH_3$ | OH | H | Oxal | 55 |
| 33 | $CH_3$ | H | $C_2H_5$ | $C_2H_5$ | H | OH | H | — | wax |
| 34 | $CH_3$ | H | $C_2H_5$ | $C_2H_5$ | H | OH | H | Oxal | 172–174 |
| 35 | $C_2H_5$ | $CH_3$ | $C_2H_5$ | $CH_3$ | H | OH | H | — | |
| 36 | $C_2H_5$ | $CH_3$ | $C_2H_5$ | $CH_3$ | H | OH | H | HCl | 119–120 |
| 37+ | $CH_3$ | $CH_3$ | $CH_3$ | $C_2H_5$ | H | OH | H | — | wax |
| 38+ | $CH_3$ | $CH_3$ | $C_2H_5$ | $C_2H_5$ | H | OH | H | HCl | 143 |
| 39− | $CH_3$ | $CH_3$ | $C_2H_5$ | $C_2H_5$ | H | OH | H | — | wax |
| 40− | $CH_3$ | $CH_3$ | $C_2H_5$ | $C_2H_5$ | H | OH | H | HCl | 138–142 |
| 41 | $CH_3$ | $CH_3$ | $C_2H_5$ | H | H | OH | H | — | 95 |
| 42 | $CH_3$ | $CH_3$ | $C_2H_5$ | H | H | OH | H | Oxal | 232–233 |
| 43 | $CH_3$ | $CH_3$ | H | $CH_2=CHCH_2$— | H | OH | H | — | 65 |
| 44 | $CH_3$ | $CH_3$ | H | $CH_2=CHCH_2$— | H | OH | H | Oxal | 222 |
| 45 | $CH_3$ | $CH_3$ | | —$(CH_2)_5$— | H | OH | H | — | 52 |
| 46 | $CH_3$ | $CH_3$ | | —$(CH_2)_5$— | H | OH | H | Oxal | 184–186 |
| 47 | $CH_3$ | $CH_3$ | | —$(CH_2)_3$— | H | OH | H | — | oil |
| 48 | $CH_3$ | $CH_3$ | | —$(CH_2)_3$— | H | OH | H | Oxal | 156 |
| 49 | $CH_3$ | $CH_3$ | $C_2H_5$ | $iC_3H_7$ | H | OH | H | — | oil |
| 50 | $CH_3$ | $CH_3$ | $C_2H_5$ | $iC_3H_7$ | H | OH | H | Oxal | 46–48 |
| 51 | $CH_3$ | $CH_3$ | $CH_3$ | n-$C_6H_{13}$ | H | OH | H | — | oil |
| 52 | $CH_3$ | $CH_3$ | $CH_3$ | n-$C_6H_{13}$ | H | OH | H | Oxal | 106–108 |
| 53 | $CH_3$ | $CH_3$ | H | H | H | OH | H | — | 73 |
| 54 | $CH_3$ | $CH_3$ | H | H | H | OH | H | Oxal | 181 |
| 55 | $CO_2C_2H_5$ | $CH_3$ | $C_2H_5$ | $C_2H_5$ | H | OH | H | HCl | wax |
| 56 | $CO_2C_2H_5$ | $CH_3$ | $C_2H_5$ | $C_2H_5$ | H | OH | H | HCl | 190 |
| 57 | $CH_3$ | $CH_3$ | $C_2H_5$ | $C_2H_5$ | H | H | H | — | wax |
| 58 | $CH_3$ | $CH_3$ | $C_2H_5$ | $C_2H_5$ | H | H | H | Oxal | 158–160 |
| 59 | $CH_3$ | $CH_3$ | $C_2H_5$ | $C_2H_5$ | H | H | H | HCl | 192 |
| 60 | $C_2H_5$ | $C_6H_5$ | $C_2H_5$ | $C_2H_5$ | H | H | H | — | wax |
| 61 | $C_2H_5$ | $C_6H_5$ | $C_2H_5$ | $C_2H_5$ | H | H | H | HCl | 168–169 |
| 62 | $CH_3$ | $CH_3$ | $C_2H_5$ | i-$C_3H_7$ | 5-F | OH | H | — | oil |
| 63 | $CH_3$ | $CH_3$ | $C_2H_5$ | i-$C_3H_7$ | 5-F | OH | H | HCl | 169 |
| 64 | $C_2H_5$ | $CH_3$ | $C_2H_5$ | i-$C_3H_7$ | H | OH | H | — | oil |
| 65 | $C_2H_5$ | $CH_3$ | $C_2H_5$ | i-$C_3H_8$ | H | OH | H | HCl | 115 |
| 66 | $C_2H_5$ | $C_2H_5$ | $C_2H_5$ | i-$C_3H_8$ | H | OH | H | — | oil |
| 67 | $C_2H_5$ | $C_2H_5$ | $C_2H_5$ | i-$C_3H_8$ | H | OH | H | HCl | 158–160 |
| 68 | $C_2H_5$ | $CH_3$ | $C_2H_5$ | $C_2H_5$ | 5-F | OH | H | — | oil |
| 69 | $C_2H_5$ | $CH_3$ | $C_2H_5$ | $C_2H_5$ | 5-F | OH | H | HCl | 167 |
| 70 | $C_2H_5$ | $CH_3$ | $C_2H_5$ | i-$C_3H_8$ | 5-F | OH | H | — | oil |
| 71 | $C_2H_5$ | $CH_3$ | $C_2H_5$ | i-$C_3H_8$ | 5-F | OH | H | HCl | 147 |
| 72 | $CO_2N(CH_3)_2$ | $CH_3$ | $C_2H_5$ | $C_2H_5$ | H | OH | H | — | oil |
| 73 | $CO_2N(CH_3)_2$ | $CH_3$ | $C_2H_5$ | $C_2H_5$ | H | OH | H | HCl | 132 |
| 74 | $CO_2NH_2$ | $CH_3$ | $C_2H_5$ | $C_2H_5$ | H | OH | H | — | oil |
| 75 | $CO_2NH_2$ | $CH_3$ | $C_2H_5$ | $C_2H_5$ | H | OH | H | HCl | 216 |
| 76 | $CO_2H$ | $CH_3$ | $C_2H_5$ | $C_2H_5$ | H | OH | H | — | oil |
| 77 | $CO_2H$ | $CH_3$ | $C_2H_5$ | $C_2H_5$ | H | OH | H | HCl | 270 |
| 78 | CN | $CH_3$ | $C_2H_5$ | $C_2H_5$ | H | OH | H | — | oil |
| 79 | CN | $CH_3$ | $C_2H_5$ | $C_2H_5$ | H | OH | H | HCl | 181 |

| | | | | | | | | | |
|---|---|---|---|---|---|---|---|---|---|
| 80 | CHF$_2$ | CH$_3$ | C$_2$H$_5$ | C$_2$H$_5$ | H | OH | H | — | oil |
| 81 | CHF$_2$ | CH$_3$ | C$_2$H$_5$ | C$_2$H$_5$ | H | OH | H | HCl | 107 |
| 82 | CH$_2$F | CH$_3$ | C$_2$H$_5$ | C$_2$H$_5$ | H | OH | H | — | oil |
| 83 | CH$_2$F | CH$_3$ | C$_2$H$_5$ | C$_2$H$_5$ | H | OH | H | HCl | 160 |
| 84 | C$_2$F$_5$ | CH$_3$ | C$_2$H$_5$ | C$_2$H$_5$ | H | OH | H | — | oil |
| 85 | C$_2$F$_5$ | CH$_3$ | C$_2$H$_5$ | C$_2$H$_5$ | H | OH | H | HCl | 111 |
| 86 | CH$_2$OH | CH$_3$ | C$_2$H$_5$ | C$_2$H$_5$ | H | OH | H | — | oil |
| 87 | CH$_2$OH | CH$_3$ | C$_2$H$_5$ | C$_2$H$_5$ | H | OH | H | HCl | 127–130 |
| 88 | C$_2$H$_5$ | CH$_3$ | C$_2$H$_5$ | C$_2$H$_5$ | 5-F | OH | H | — | oil |
| 89 | C$_2$H$_5$ | CH$_3$ | C$_2$H$_5$ | C$_2$H$_5$ | 5-F | OH | H | HCl | 186 |

In this table:
oxal represents a hemioxalate,
HCl represents a hydrochloride,
"—" represents a compound in the free form,
nC$_3$H$_7$ represents a linear propyl group,
iC$_3$H$_7$ represents a i-propyl group,
nC$_6$H$_{13}$ represents a linear hexyl group.

Furthermore, the compounds where the number is accompanied by a "+" are in the (+) form and those accompanied by a "−" are in the (−) form. All the other compounds in the Table are racemates.

The hydrochloride salts described in the Table were prepared in the following way:

An excess of an ethanol solution saturated with anhydrous hydrochloric acid is added to the compound according to the invention in the base form. The salt obtained is then concentrated under vacuum, recrystallized from ethyl acetate and then dried in a desiccator under vacuum over phosphorus pentoxide.

The compounds of the invention were subjected to biological tests intended to demonstrate their selective contractile activity for smooth muscles.

1. The in vitro activity of the compounds of the invention was studied on urethral and arterial smooth muscles.

These tests were carried out on female New Zealand rabbits weighing from 3 to 3.5 kg. The animals were killed by vertebral dislocation and then rings of tissue were removed from the mesenteric arteries and from the urethra. These rings of tissue were immersed in a modified Krebs solution oxygenated by a mixture of 95% O$_2$ and tissue sample was subjected to a tension of 1 g, phenylephrine was then introduced in cumulative doses and the dose/response curve was drawn up. After rinsing the samples, the compound to be studied was introduced in cumulative doses and the dose/response curve was drawn up. The contractile effect of each compound is evaluated by the calculation of the pD$_2$ (negative logarithm of the agonist concentration which induces 50% of the maximum contraction) and by the maximum effect representing the percentage of the maximum contraction obtained with phenylephrine (% E$_{max}$).

The results obtained show that the compounds in accordance with the invention exhibit:

a urethral pD$_2$ of greater than 2.5, usually of between 4 and 8, more generally of between 5 and 8, an arterial pD$_2$ of less than 3, a urethral % E$_{max}$ of more than 30, usually of between 40 and 90, an arterial % E$_{max}$ equal to zero.

2. The in vivo activity of the compounds of the invention on blood and urethral pressure was studied in the amyelous rat and the rabbit, according to the following protocols:

Pithed rats

Wistar rats are anaesthetized and pithed (according to the technique described by Gillespie, MacLaren A. and Polock D., A method of stimulating different segments of the autonomic outflow from the spinal column to various organs in the pithed cat and rat; Br. J. Pharmacol., 1970, 40: 257–267). Catheters are introduced via the aorta and a jugular vein. Another catheter is introduced into the urethra via an incision made in the bladder. The compounds to be tested are administered at increasing doses via intravenous infusion.

The results are expressed in doses (μg/kg) necessary to increase the urethral pressure by 10 cm of water (UP$_{10}$) or the arterial pressure by 10 mm of Hg (AP$_{10}$) or by 50 mm of Hg (AP$_{50}$). The compounds of the invention, thus tested, made it possible to obtain:

a UP$_{10}$ with doses of less than 100 μg/kg, usually of between 20 and 50 μg/kg, an AP$_{10}$ with doses of greater than 110 μg/kg, usually of between 130 and 250 μg/kg, the AP$_{50}$ could not be reached.

Conscious rabbits

The experiments are carried out on female New Zealand rabbits weighing between 3 and 4 kg anaesthetized by pentobarbital. The catheters are introduced via the descending part of the aorta into the femoral artery, into a jugular vein and into the urethra (1.5 cm below the neck of the bladder). The compounds to be tested are administered 5 to 15 days following the operation, by intravenous (i.v.) administration or per os (p.o.).

The compounds are administered by the i.v. route over 5 minutes in a single dose (100 μg/kg). The compounds are administered by the oral route by force-feeding at a dose of 3 mg/kg. In this instance, the increase in the urethral pressure (UP) and in the arterial pressure (AP) were measured with respect to the urethral basal pressure and the arterial basal pressure respectively. The results obtained are expressed as percentage of premedication values at 5 minutes after dosing.

The compounds of the invention, thus tested, made possible an increase in the UP of more than 70%, usually of between 90 and 25%. The increase in the AP was always less than 10% and was usually 0%.

The combined results above show that the compounds of the invention have a strong urethral action and a weak arterial action.

It could be determined that the compounds of the invention were ligands of α-adrenergic receptors but not of β-adrenergic receptors.

They can be used as a medicament, in particular as an agent for contracting smooth muscles, and more particularly still in the treatment of urinary incontinence, in particular urinary stress incontinence. In this indication, the compounds according to the invention are highly effective and usually exhibit fewer side effects than the medicaments conventionally used for such a treatment, in particular as regards side effects affecting the arteries.

The compounds of the invention were subjected to biological tests intended to demonstrate their venoconstrictive activity.

1. The in vitro activity of the compounds of the invention was studied on the saphenous veins of the Yucatan miniature pig. The tissue is cut into a helix and mounted in an isolated organ tank in a modified Krebs solution oxygenated by a mixture of 95% $O_2$ and 5% $CO_2$ held at 37° C. The vessel is connected to an isometric sensor under a basal tension of 1 g and connected to a polygraph which makes it possible to record variations in tension. The viability of each preparation is tested by prestimulation with 3 μM noradrenaline. After rinsing, the compound to be studied is introduced and its concentration/response curve constructed cumulatively until a maximum response is obtained. The contractile effect of each compound is evaluated by calculation of the $EC_{50}$ (concentration producing 50% of the maximum response).

The compounds of the invention have made it possible to obtain a venoconstrictive activity with an $EC_{50}$ value usually of between 1 μM and 100 μM.

The compounds of the invention can be used in the treatment of venous insufficiency and of venous ulcers.

The compounds according to the invention can also be employed in the treatment of migraine or gastrointestinal disorders and as vasoconstrictor of the nasal mucous membrane.

The compounds according to the invention can be presented in various pharmaceutical forms appropriate for oral administration and for topical application, if appropriate in combination with at least one pharmaceutical excipient. The appropriate pharmaceutical forms are, for example, tablets, capsules, including hard gelatin capsules, sugar-coated tablets, solutions to be taken orally, injectable solutions, syrups or suppositories. These pharmaceutical forms can contain a dose which makes possible a daily dose of 0.1 μg/kg to 50 mg/kg.

Appendix

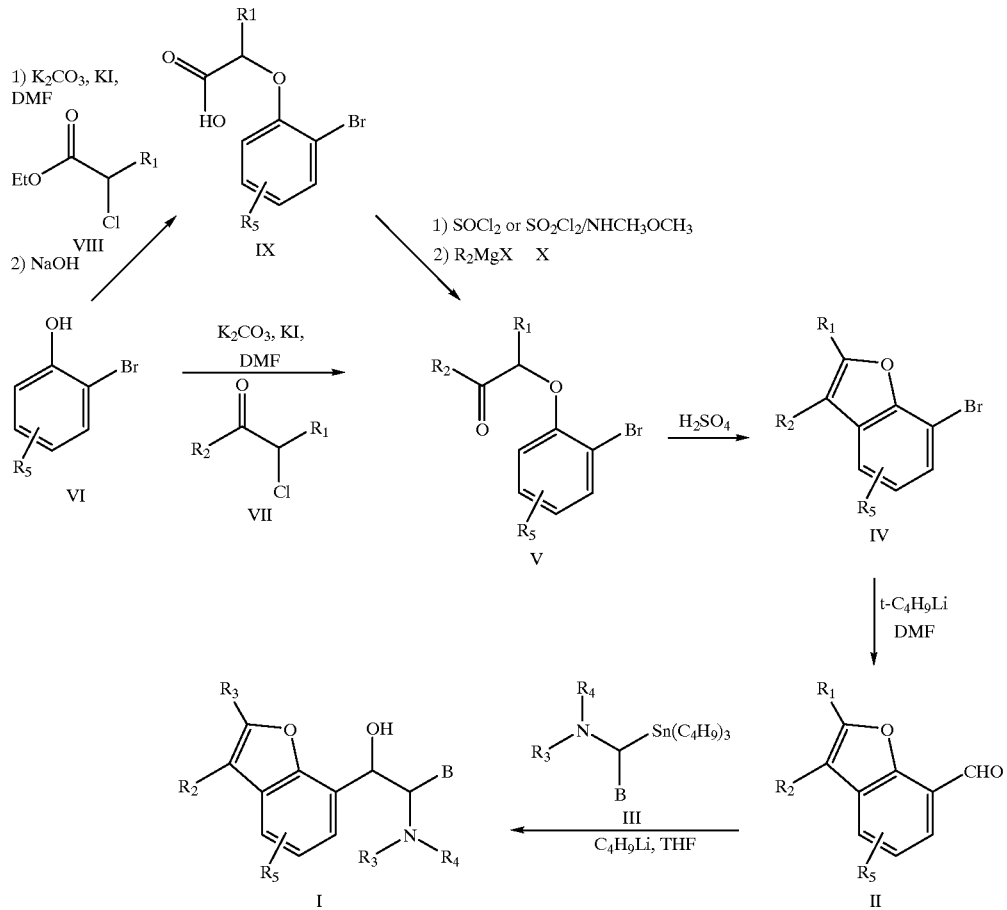

What is claimed is:
1. A compound of formula (I)

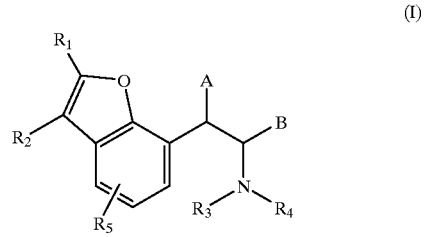

in which:
A represents either a hydrogen atom or a hydroxyl group,
B represents either a hydrogen atom or a $C_{1-8}$ alkyl, $C_{1-8}$ alkenyl, $C_{1-8}$ fluoroalkyl or $C_{1-8}$ perfluoroalkyl group,
$R_1$, $R_2$ and $R_5$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, with the proviso that when $R_1$ and $R_2$ are each a methyl group, $R_3$, $R_4$, A and B are each a hydrogen atom and $R_5$ is not a methoxy group, in the form of enantiomers or diastereoisomers or of mixtures of these forms, or of their addition salts with pharmaceutically acceptable acids.

2. Process for the preparation of a compound of formula (I)

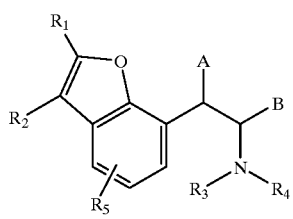

in which:

A represents either a hydrogen atom or a hydroxyl group,

B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$, $R_2$ and $R_5$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, in the form of enantiomers or diastereoisomers or of mixtures of these forms, or of their addition salts with pharmaceutically acceptable acids comprising reacting an aldehyde of formula II

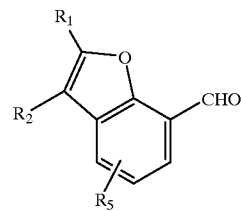

with an (aminoalkyl)stannate derivative of formula III

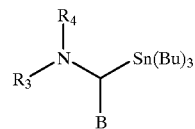

the meanings of $R_1$, $R_2$, $R_3$, $R_4$, $R_5$ and B of the aldehyde of formula II and of the (aminoalkyl)stannate derivative of formula III being those defined for the compound of formula (I).

3. Process for the preparation of a compound of formula (I)

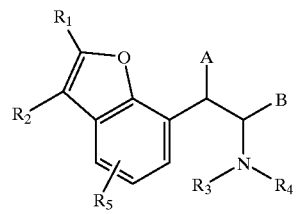

in which:

A represents a hydroxyl group,

B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$, $R_2$ and $R_5$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, in the form of enantiomers or diastereoisomers or of mixtures of these forms, or of their addition salts with pharmaceutically acceptable acids comprising reacting an oxirane derivative of formula XVI

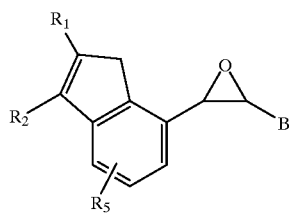

with an amine of formula $NHR_3R_4$, the meanings of $R_1$, $R_2$, $R_5$ and B of the oxirane of formula XVI and of $R_3$ and $R_4$ of the amine being those defined for the compound of formula (I).

4. Process for the preparation of a compound of formula (I)

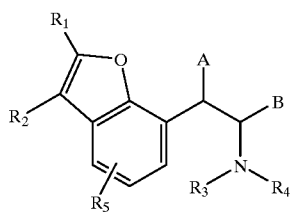

in which:

A represents a hydrogen atom,

B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$ and $R_2$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, $R_5$ represents a hydrogen atom in the form of enantiomers or diastereoisomers or of mixtures of these forms, or of their addition salts with pharmaceutically acceptable acids comprising reacting a compound of formula XIX

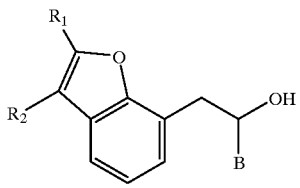

with an amine of formula $NHR_3R_4$ after activation of the hydroxyl group into a nucleophuge group, the meanings of $R_1$, $R_2$, $R_3$, $R_4$ and B of the compound of formula XIX and of the amine being those defined for the compound of formula (I).

5. A method of treating a patient for urinary incontinence, venous insufficienicy, venous ulcers, migraines or gastrointestinal disorders comprising administering to a patient in need thereof an effective amount of a compound of formula (I)

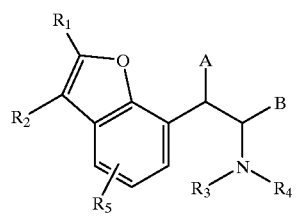

in which:

A represents either a hydrogen atom or a hydroxyl group,

B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$, $R_2$ and $R_5$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, in the form of enantiomers or diastereoisomers or of mixtures of these forms, or of their addition salts with pharmaceutically acceptable acids.

6. Pharmaceutical composition, comprising an effective amount of a compound of formula (I)

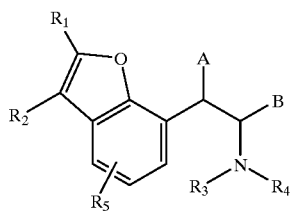

(I)

in which:

A represents either a hydrogen atom or a hydroxyl group,

B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$, $R_2$ and $R_5$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, in the form of enantiomers or diastereoisosmers or of mixtures of these forms, or of their addition salts with pharmaceutically acceptable acids and one or more excipients.

7. Compound according to claim 1, wherein the halogen atom represented by $R_1$, $R_2$ and $R_5$ is chlorine, bromine or fluorine.

8. Compound according to claim 1, wherein the cycloalkenyl ring represented by $R_3$ and $R_4$ together is a piperidyl, azetidinyl or pyrrolidyl ring.

9. Compound according to claim 1 wherein the mixtures are racemic mixtures.

10. Process according to claim 4, wherein the hydroxyl group is activated by mesyl chloride.

11. A compound of formula (I)

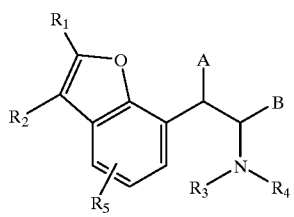

(I)

in which:

A represents either a hydrogen atom or a hydroxyl group,

B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$, $R_2$ and $R_5$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group with the exclusion of compounds in which $R_5$ represents $C_{1-6}$ alkoxy, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, in the form of enantiomers or diastereoisomers or of mixtures of these forms, or of their addition salts with pharmaceutically acceptable acids.

12. A compound of formula (I)

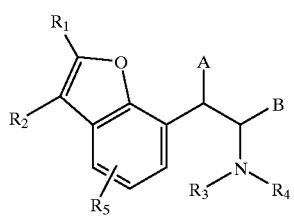

(I)

in which:

A represents either a hydrogen atom or a hydroxyl group,

B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$ and $R_2$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, $R_5$ represents a hydrogen atom in the form of enantiomers or diastereoisomers or of mixtures of these forms, or of their addition salts with pharmaceutically acceptable acids.

13. A compound of formula (I)

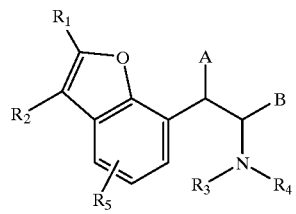

in which:

A represents a hydroxyl group,

B represents either a hydrogen atom or a $C_{1-8}$ alkyl, $C_{1-8}$ alkenyl, $C_{1-8}$ fluoroalkyl or $C_{1-8}$ perfluoroalkyl group, $R_1$, $R_2$ and $R_5$, which are identical or different, each represent a hydrogen atom, a halogen atom, or a $C_{1-8}$ alkyl, $C_{1-8}$ alkenyl, $C_{3-8}$ cycloalkyl, $C_{3-8}$ cycloalkenyl, $C_6$, $C_{10}$ or $C_{14}$ aryl, $C_{1-6}$ alkoxycarbonyl, $C_{1-6}$ hydroxyalkyl, $C_{1-6}$ alkoxyalkyl, $C_{1-6}$ alkoxy, $C_{1-8}$ fluoroalkyl or $C_{1-8}$ perfluoroalkyl group, or $R_1$ and $R_2$ together form a $C_{3-8}$ cycloalkyl, $C_{3-8}$ cycloalkenyl or $C_6$, $C_{10}$ or $C_{14}$ aryl ring, with the exclusion of the compounds in which $R_1$ and $R_2$ are simultaneously hydrogens and of 1-(dibenzofuran-2-yl)-2-isopropylaminoethanol, $R_3$ and $R_4$, which are identical or different, represent either a hydrogen atom or a $C_{1-8}$ alkyl, $C_{1-8}$ alkenyl, $C_{3-8}$ cycloalkyl or $C_{3-8}$ cycloalkenyl group, or $R_3$ and $R_4$ together form a $C_{3-6}$ cycloalkyl or $C_{3-6}$ cycloalkenyl ring, in the form of enantiomers or diastereoisomers or of mixtures of these forms, or of their addition salts with pharmaceutically acceptable acids.

14. A compound of formula (I)

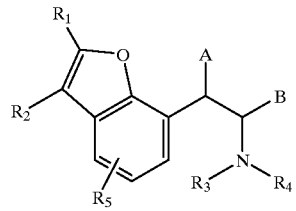

in which:

A represents a hydroxyl group,

B represents a hydrogen atom, $R_1$ and $R_2$ each represent a $C_{1-4}$ alkyl group or a $CF_3$ group, or $R_1$ and $R_2$ together form a $C_{3-6}$ cycloalkyl group, $R_3$ and $R_4$ each represent a $C_{1-4}$ alkyl group, in the form of enantiomers or diastereoisomers or of mixtures of these forms, or of their addition salts with pharmaceutically acceptable acids.

* * * * *